United States Patent
Brown et al.

(10) Patent No.: US 7,468,453 B2
(45) Date of Patent: Dec. 23, 2008

(54) PRODUCTION PROCESS OF GAMMA-CYHALOTHRIN

(75) Inventors: Stephen Martin Brown, Huddersfield (GB); Brian David Gott, Huddersfield (GB)

(73) Assignee: Syngenta Limited (GB)

( * ) Notice: Subject to any disclaimer, the term of this patent is extended or adjusted under 35 U.S.C. 154(b) by 541 days.

(21) Appl. No.: 10/539,265

(22) PCT Filed: Dec. 9, 2003

(86) PCT No.: PCT/GB03/05450

§ 371 (c)(1), (2), (4) Date: Jun. 16, 2005

(87) PCT Pub. No.: WO2004/056752

PCT Pub. Date: Jul. 8, 2004

(65) Prior Publication Data

US 2006/0100457 A1    May 11, 2006

(30) Foreign Application Priority Data

Dec. 20, 2002 (GB) .................................. 0229803.2

(51) Int. Cl.
*C07C 255/32* (2006.01)
*C07C 255/35* (2006.01)

(52) U.S. Cl. ...................... 558/404; 558/303; 558/388; 558/406; 558/407

(58) Field of Classification Search ................ 558/303, 558/388, 404, 406, 407
See application file for complete search history.

(56) References Cited

U.S. PATENT DOCUMENTS

| 3,835,176 | A | 9/1974 | Matsuo et al. |
| 4,133,826 | A | 1/1979 | Warnant et al. |
| 4,183,948 | A | 1/1980 | Huff |
| 4,427,598 | A | 1/1984 | Mason et al. |
| 4,436,667 | A | 3/1984 | Bull |
| 4,512,931 | A | 4/1985 | Robson |
| 4,544,510 | A | 10/1985 | Berkel et al. |
| 4,681,969 | A | 7/1987 | Williams et al. |
| 4,997,970 | A | 3/1991 | Ager, Jr. |
| 5,128,497 | A | 7/1992 | Ager |
| 5,334,744 | A | 8/1994 | Cleugh et al. |

FOREIGN PATENT DOCUMENTS

| EP | 0106469 | 4/1984 |
| GB | 2000764 | 1/1979 |
| GB | 2000764 A | 1/1979 |
| IN | 178538 | 5/1997 |

OTHER PUBLICATIONS

Danish Academy of Technical Sciences: "Target Molecules - Design, Optimisation and Production (and List of participants)" The Knud Lind Larsen Symposium Jan. 25, 2002 - Jan. 26, 2002, pp. 1-10, XP002991488.

Danish Academy of Technical Sciences: 'Partial Content of PowerPoint presentation on Target Molecules' The Knud Lind Larsen Symposium Jan. 25, 2002 - Jan. 26, 2002, pp. 1-10, XP002991489.

*Primary Examiner*—Golam M. M. Shameem
(74) *Attorney, Agent, or Firm*—Rebecca Howard

(57) ABSTRACT

A process for the preparation of gamma-cyahlothrin comprising a) chlorinating 1R cis-Z 3-(2-chloro-3,3,3-trifluoro-1-propenyl)-2,2-dimethyl cyclopropanecarboxylic acid to give 1R cis-Z 3-(2-chloro-3,3,3-trifluoro-1-propenyl)-2,2-dimethyl cyclopropanecarboxylic acid chloride; b) esterifying 1R cis-Z 3-(2-chloro-3,3,3-trifluoro-1-propenyl)-2,2-dimethyl cyclopropanecarboxylic acid chloride with 3-phenoxy benzaldehyde in the presence of a source of cyanide to form a diastereoisomeric mixture of cyhalothrin isomers and c) epimerising the diastereoisomeric mixture under conditions in which the least soluble diastereoisomer crystallises from solution.

4 Claims, No Drawings

PRODUCTION PROCESS OF GAMMA-CYHALOTHRIN

This application is a 371 of International Application No. PCT/GB2003/005450 filed Dec. 9, 2003, which claims priority to GB 0229803.2, filed Dec. 20, 2002, the contents of which are incorporated herein by reference.

The present invention relates to a process for making insecticidal cyclopropanecarboxylic acid esters. More particularly, the invention relates to a process for making gamma-cyhalothrin [(S)-α-cyano-3-phenoxybenzyl (Z)-(1R,3R)-3-(2-chloro-3,3,3-trifluoro-1-propenyl)-2,2-dimethylcyclopropanecarboxylate].

It is well known that the insecticidal activity of pyrethroids such as cyclopropane-carboxylic acid esters e.g. cyhalothrin is greatly affected by their stereochemistry. It is disclosed in Bentley et al, Pestic. Sci. (1980), 11(2), 156-64) that (S)-α-cyano-3-phenoxybenzyl (Z)-(1R,3R)-3-(2-chloro-3,3,3-trifluoro-1-propenyl)-2,2-dimethylcyclopropanecarboxylate is the most active isomer of cyhalothrin.

Known processes for making gamma-cyhalothrin, such as those outlined in GB2000764 and EP132392, involve esterification of 1R cis-Z 3-(2-chloro-3,3,3-trifluoro-1-propenyl)-2,2-dimethyl cyclopropanecarboxylic acid with an optically active cyanohydrin. However on an industrial scale it is preferable to find alternative methods of making the final product that avoid the use of the very expensive cyanohydrin.

There is therefore provided a process for the preparation of gamma-cyhalothrin comprising a) chlorinating 1R cis-Z 3-(2-chloro-3,3,3-trifluoro-1-propenyl)-2,2-dimethyl cyclopropanecarboxylic acid (V) to give 1R cis-Z 3-(2-chloro-3,3,3-trifluoro-1-propenyl)-2,2-dimethyl cyclopropanecarboxylic acid chloride (III); b) esterifying 1R cis-Z 3-(2-chloro-3,3,3-trifluoro-1-propenyl)-2,2-dimethyl cyclopropanecarboxylic acid chloride (III) with 3-phenoxy benzaldehyde (IV) in the presence of a source of cyanide to form a diastereoisomeric mixture of 1R cyhalothrin isomers (II) and c) epimerising the diastereoisomeric mixture (II) under conditions in which the least soluble diastereoisomer (I) crystallises from solution.

1R cis-Z 3-(2-chloro-3,3,3-trifluoro-1-propenyl)-2,2-dimethyl cyclopropanecarboxylic acid (V) is a known compound and its preparation is described for example in U.S. Pat. No. 4,683,089, WO02/06202, WO97/03941 and WO/9942432.

Step a) is performed by standard techniques as in 'March 4$^{th}$ Edition-p437-38'. Preferred chlorinating agents are thionyl chloride, phosgene or phosphorous oxychloride.

It is preferred that solvents used in the process are hydrocarbons such as toluene, hexane, heptane or fluorobenzene.

Preferred temperatures for the process are from ambient to 100° C. or the boiling point of the solvent Preferably the acid (V) has an enantiomeric purity of greater than 80% of 1R 3R enantiomer, and most preferably greater than 90% 1R 3R enantiomer.

Step b) is performed in the presence of a cyanide source. Suitable sources of cyanide are alkali or alkaline earth metal cyanides, but preferably an alkali metal cyanide and more preferably sodium cyanide.

The reaction can be carried out in a solvent or in a mixture of a water immiscible solvent and an aqueous solution of the source of cyanide or in the absence of a solvent. Suitable solvents are aliphatic or aromatic hydrocarbons solvents. Examples of aromatic hydrocarbons are toluene, o-xylene, mixed xylenes or halobenzenes, for example fluorobenzene. Aliphatic hydrocarbons are for example hexane, iso-hexane, heptane, octane or mixtures of hydrocarbons commonly known as petroleum ethers. Preferred solvents are hexane, iso-hexane, heptane or octane.

The acid chloride (III) and 3-phenoxybenzaldehyde (IV) can be added sequentially or simultaneously to the source of cyanide in the presence of the solvent or the solvent mixture, optionally in presence of an organic base or an onium salt.

Alternatively, the source of cyanide may be added to a mixture of the acid chloride (III) and 3-phenoxybenzaldehyde in the presence of a solvent, optionally in the presence of water, if a water-immiscible solvent is used, and optionally in the presence of an organic base or an onium salt.

Suitably, the source of cyanide is used in excess, preferably between 1.0 and 2.0 molar equivalents on the acid chloride and most preferably 1-1.5 equivalents.

The aldehyde (IV) is used in substantially stoichiometric amounts, but may be used in a slight excess of up to 0.10 equivalents on the acid chloride.

The organic base is preferably a tertiary amine, such as triethylamine, triisopropylamine, or a tertiary diamine such as tetramethylethylene diamine, 1,4-diazabicyclo[2,2,2]octane or 1,4-diazabicyclo[5.4.0]undec-7-ene. The base can be used in sub-stoichiometric amounts, preferably 0-50 mol % on the acid chloride and most preferably 1-10 mol %. The onium salt can be a quaternary ammonium salt, such as tetra n-butylammonium bromide, or a phosphonium salt or a sulphonium or sulphoxonium salt, and is used in similar proportions as the organic base.

The reaction can be carried out at between −10° C. and the boiling point of the solvent system, preferably between 0° C. and 60° C. and most preferably between 0° C. and 20° C.

The compound of formula (II) may be isolated and purified or used directly in step c) without isolation or purification.

The compound of formula (II) is a mixture of (S)-α-cyano-3-phenoxybenzyl (Z)-(1R,3R)-3-(2-chloro-3,3,3-trifluoro-1-propenyl)-2,2-dimethylcyclopropanecarboxylate and (R)-α-cyano-3-phenoxybenzyl (Z)-(1R,3R)-3-(2-chloro-3,3,3-trifluoro-1-propenyl)-2,2-dimethylcyclopropanecarboxylate and is novel and as such it forms a further aspect of the invention.

Compound (IV), 3-phenoxy benzaldehyde, is a commercially available compound

Step c) may also be carried out in a solvent and a source of cyanide. The solvent and the source of cyanide are preferably those used in step b) although the cyanide need only be present in catalytic amounts, typically from 1-10 mol %. The organic base optionally present in step b) may also be optionally present. Step c) may be carried out in the presence of a seed of gamma-cyhalothrin where the seed is present in an amount of between 1% and 90% of the amount of the 1R cyhalothrin entering step c). The seed is preferably dispersed in the solvent before cooling at the start of step c), or may be the retained crystallization mass from a previous execution of step c).

The reaction is performed at −20° C. to 50° C., preferable −20° C. to 30° C. and most preferably −10° C. to 10° C. On completion of the reaction, the slurry can be filtered to recover the gamma-cyhalothrin, preferably having first added an acid to arrest the epimerisation reaction. The acid can be a mineral acid such as hydrochloric acid or sulphuric acid or an organic acid such as formic or acetic acid and is used in at least stoichiometric amounts on the total bases present in the system, i.e. the organic base plus any residual source of cyanide, and preferably in twice stoichiometric amounts. The solid gamma-cyhalothrin can be washed and dried by conventional methods. Alternatively, the slurry of gamma-cyhalothrin in the reaction mixture after addition of acid can be heated to dissolve the product, washed with water to remove catalysts and salts and the aqueous phase removed by separation. As appreciated by those skilled in the art, the pH of any water washes can be adjusted to facilitate removal of acid or basic catalysts or by-product species added or formed during the process. The gamma-cyhalothrin can then be recovered from the solvent layer by, for example, cooling, crystallization and filtration, or by evaporation of the solvent.

Surprisingly, the applicants have also found it is possible to make gamma-cyhalothrin in a process wherein steps b) and c) can be combined (in a one-pot process), that is a process for the preparation of gamma-cyhalothrin in which 1R cis-Z 3-(2-chloro-3,3,3-trifluoro-1-propenyl)-2,2-dimethyl cyclopropanecarboxylic acid chloride (III) is reacted with 3-phenoxy benzaldehyde (IV) and a source of cyanide to give gamma-cyhalothrin (I).

The reaction is performed in a single step and does not require the isolation of the mixture of diastereomers (II) formed in the initial esterification. This embodiment has the advantage of reducing solvent recovery/waste disposal, of enabling higher productivity with less equipment and of reducing impurity formation due to the avoidance of reactive solvents and reduced work-up times.

It is preferred to carry out the reaction in a solvent.

In the combined process, once the esterification is complete, as judged by analysis, it is advantageous to remove any aqueous phase, after adjusting the pH to between pH 9-13, by warming the reaction mixture to 20° C.-60° C. and separation, before substantial amounts of epimerisation and crystallization of gamma-cyhalothrin takes place. The pH can be adjusted with addition of an inorganic base such as sodium hydroxide or sodium carbonate. The reaction mixture can then be cooled to the preferred epimerisation and crystallization temperature to complete the process. Optionally the organic base, or an onium salt and additional source of cyanide can be added after the esterification, pH adjustment and separation but before substantial amounts of epimerisation and crystallization of gamma-cyhalothrin has taken place. In this situation, the cyanide need only be added in catalytic amounts, typically from 1-10 mol %.

The following Examples illustrate the invention.

The products were analysed by Gas Chromatography using an Agilent gas chromatograph with a Chrompack CP Sil 5 CB column (50 meters, 0.32 mm ID and 0.1 μm film thickness) with helium as carrier, split injection at 15 psi. Injection temperature 300° C. detector 325° C. and a detector gas composition of hydrogen 30 ml/min, air 350 ml/min and helium at 30 ml/min). The oven temperature profile was: initial temp 50° C., initial time 6 mins then heating rate 10° C. min to 120° C. and hold for 3 mins then ramp to 240° C. at 25° C./min. Hold for 8 minutes then ramp to 300° C. at 50° C. and hold for 6 minutes to burn off the column.

Using these conditions, the following retention times were observed:

(S)-α-cyano-3-phenoxybenzyl (Z)-(1R,3R)-3-(2-chloro-3,3,3-trifluoro-1-propenyl)-2,2-dimethylcyclopropanecarboxylate (gamma-cyhalothrin) 27.4 mins (R)-α-cyano-3-phenoxybenzyl (Z)-(1R,3R)-3-(2-chloro-3,3,3-trifluoro-1-propenyl)-2,2-dimethylcyclopropanecarboxylate 27.0 mins

EXAMPLE 1

Preparation of 1R cis-Z 3-(2-chloro-3,3,3-trifluoro-1-propenyl)-2,2-dimethyl-cyclopropane carboxylic acid chloride A 1 liter dry, clean jacketed split reaction vessel equipped with agitator, thermometer, condenser, nitrogen blanket and vent to a scrubber system was charged with toluene (450 ml) and agitated whilst 1R cis-Z 3-(2-chloro-3,3,3-trifluoro-1-propenyl)-2,2-dimethyl-cyclopropane carboxylic acid (89.4 gm=0.369 mol) was added followed by triethylamine (0.21 gm=2.1 mmol). The reaction mixture was then heated to 45° C., using oil circulation on the jacket, and thionyl chloride (62.0 gm=0.52 mol) was then charged over 105 minutes maintaining on temperature. The reaction mass was then agitated for 5 hours at 45° C. then tested by GLC for completion of reaction showing 2% residual acid. A further addition of thionyl chloride (4.4 gm=37 mmol) was then made and the reaction mass allowed to cool with stirring overnight. The following day, residual thionyl chloride, dissolved sulphur dioxide and hydrogen chloride gases were removed by distillation of about 320 ml toluene under vacuum. GC, GCMS and NMR analysis of the product were consistent with the structure of the acid chloride (IIIa). Yield, 175 gm of a 54% solution of the acid chloride in toluene, ~97% theory. $\alpha_D$=+46° (c=0.012, DCM).

EXAMPLE 2

Preparation of 1R Cyhalothrin (II)

A 2 liter jacketed non-baffled split-neck reaction flask was equipped with an overhead stirrer (turbine), thermometer, condenser, two syringe pumps and was vented to a caustic/hypochlorite scrubber. To the reactor was charged sodium cyanide (29.4 g, 0.59 mol) in water (101 ml) and the reaction was agitated (100 rpm) for 10 min to ensure complete dissolution of the cyanide. Hexane (79 ml) was added to the reactor, then the reaction mass was cooled to 10° C. and the agitation rate adjusted to 235 rpm. 1R cis-Z 3-(2-chloro-3,3, 3-trifluoro-1-propenyl)-2,2-dimethyl cyclopropanecarboxylic acid chloride (133.2 g, 0.50 mol) and 3-phenoxybenzaldehyde (99 g, 0.50 mol) were added simultaneously to the reactor over 3 hr. Once the addition was complete the reaction was agitated for a further 17 hr at 10° C. GC analysis indicated the presence of un-reacted 3-phenoxybenzaldehyde, so a further charge of 1R cis-Z 3-(2-chloro-3,3,3-trifluoro-1-propenyl)-2,2-dimethyl cyclopropanecarboxylic acid chloride was made (3.6 g, 0.014 mol) and the reaction agitated for a further 2 hr. The reaction mass was diluted with hexane (156 ml), and the aqueous layer allowed to settle before separation. Residual cyanide in the organic phase was destroyed with sodium hypochlorite liquor to a positive show on starch/iodide paper. The positive show for hypochlorite was removed with sodium bisulphite and the aqueous phase again settled and separated. The product oil weighed 228 g giving a yield of 97.8%. The composition of the product was—1R cis-Z-α-S diastereomer 45.5% and 1R cis-Z-α-R diastereomer 45.9%. GCMS (both diastereomers); 449 (M+), 349, 225, 208, 197, 181, 141 $[\alpha]_D^{20}$: +29.8° (c=0.0104, DCM)

EXAMPLE 3

Preparation of Gamma-Cyhalothrin

A 600 ml vacuum jacketed non-baffled split-neck reaction flask was equipped with a dual blade agitator. To the reactor, already containing a slurry of epimerisation mass as seed from a previous experiment (already~⅔rds full), was charged the 1 R cyhalothrin (II) (166.3 g) in a mixture of isopropanol (99.9 g), water (3.09 g) and di-isopropylamine (5.22 g). The reaction mass was agitated at 100 rpm and −5° C. for 65 hr, before removing 251 g of reaction mass and transferring it to a 1 liter split-neck reaction vessel in an ice/water bath. To the 1 liter reaction vessel was charged hexane (60 ml) and sulphuric acid (47 ml of 50% w/w), and the resultant thick paste was agitated for 0.5 hr before diluting with hexane (350 ml) and water (350 ml). The mixture was heated to 55° C. for 30 min, then transferred to a separating funnel and the lower aqueous phase was separated off. The hexane solution was concentrated under reduced pressure to give the desired product as a viscous red/brown oil which solidified upon standing to give an off-white solid. The product weighed 151.2 g giving an estimated yield of 97% as gamma-cyhalothrin and a diastereomer ratio of 95:5.

$^1$H NMR (CDCl$_3$): 1.20 (s, 3H, cyclopropane C$\underline{H}_3$), 1.30 (s, 3H, cyclopropane C$\underline{H}_3$), 2.00 (d, 1H, C$\underline{H}$CO$_2$), 2.25 (t, 1H, C$\underline{H}$CH=CClCF$_3$), 6.35 (s, 1H, C$\underline{H}$CN), 6.80 (d, 1H, C$\underline{H}$=CClCF$_3$), 7.00-7.50 (m, 9H, ArH).

GCMS; 449 (M+), 349, 225, 208, 197, 181, 141.

$[\alpha]_D^{20}$: +36.6° (c=0.0075, DCM)

EXAMPLE 4

One-pot Process for Gamma-Cyhalothrin

Sodium cyanide (253 gm) and water (599 ml) were charged to a 5 liter baffled reactor fitted with turbine, agitator and thermometer. The reactor contents were gently agitated to dissolve the cyanide crystals and hexane added (460 ml). The contents of the reactor were then cooled to +6° C. by applying coolant to the jacket and 3-phenoxy benzaldehyde (544 gm) and 1R cis-Z 3-(2-chloro-3,3,3-trifluoro-1-propenyl)-2,2-dimethyl cyclopropanecarboxylic acid chloride (736 gm) were added to the reaction mass over a period of 8 hours. The resultant emulsion was then stirred overnight to complete the reaction. The solid that had formed in the reaction flask was broken down with a spatula and the agitation increased to mix the solids in. A thick slurry was produced. A small sample (~4 ml) of the slurry was filtered and the paste given a token hexane wash then pulled dry. The solid (0.7884 gm) produced was a fine white crystalline material. GC analysis of the solid showed it to be gamma-cyhalothrin with a 1R alpha-S to 1R alpha-R ratio of 86:14. (Yield approx 33%). The reaction mixture was then diluted with hexane (950 ml) and the reactor temperature increased to +8° C. on the reactor jacket, the reaction mass being a fairly thin slurry. The following day, a 4 ml sample of reaction mass was removed and washed with hexane as before. The resultant white solid was washed with a little hexane and pulled dry. GC analysis showed that the material had a 1R alpha-S to 1R alpha-R ratio of 94:6. A total of 0.5352 gm of paste was obtained from this second filtration, which equated to a yield of approx. 32% gamma cyhalothrin. Mpt 55-58° C.

The invention claimed is:

1. A process for the preparation of gamma-cyhalothrin comprising a) chlorinating 1R cis-Z 3-(2-chloro-3,3,3-trifluoro-1-propenyl)-2,2-dimethyl cyclopropanecarboxylic acid to give 1R cis-Z 3-(2-chloro-3,3,3-trifluoro-1-propenyl)-2,2-dimethyl cyclopropanecarboxylic acid chloride; b) esterifying 1R cis-Z 3-(2-chloro-3,3,3-trifluoro-1-propenyl)-2,2-dimethyl cyclopropanecarboxylic acid chloride with 3-phenoxy benzaldehyde in the presence of a source of cyanide to form a diastereoisomeric mixture of 1R cyhalothrin isomers and c) epimerising the diastereoisomeric mixture under conditions in which the least soluble diastereoisomer crystallises from solution.

2. A process according to claim 1 wherein the source of cyanide is an alkali metal cyanide, especially sodium cyanide.

3. A process according to claim 1 wherein steps b) and c) are combined in a one pot process.

4. A semi-batch process according to claim 1 where between 1% and 90% of the one batch from step c) forms the basis for nucleation and crystallization of the following batch in step c).

* * * * *